(12) United States Patent
Fischell et al.

(10) Patent No.: US 6,540,775 B1
(45) Date of Patent: Apr. 1, 2003

(54) ULTRAFLEXIBLE OPEN CELL STENT

(75) Inventors: Robert E. Fischell, Dayton, MD (US); David R. Fischell, Fair Haven, NJ (US); Tim A. Fischell, Richland, MI (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 09/607,980

(22) Filed: Jun. 30, 2000

(51) Int. Cl.[7] .................................................. A61F 2/06
(52) U.S. Cl. ...................................................... 623/1.15
(58) Field of Search .............................. 623/1.15–1.21, 623/1.1, 1.36, 1.25, 900, 901; 606/194, 195, 200

(56) References Cited

U.S. PATENT DOCUMENTS

| | | |
|---|---|---|
| 3,657,744 A | 4/1972 | Ersek |
| 4,441,216 A | 4/1984 | Ionescu et al. |
| 4,503,569 A | 3/1985 | Dotter |
| 4,553,545 A | 11/1985 | Maass et al. |
| 4,580,568 A | 4/1986 | Gianturco |
| 4,733,665 A | 3/1988 | Palmaz |
| 4,776,337 A | 10/1988 | Palmaz |
| 4,800,882 A | 1/1989 | Gianturco |
| 4,856,516 A | 8/1989 | Hillstead |
| 4,886,062 A | 12/1989 | Wiktor |
| 4,907,336 A | 3/1990 | Gianturco |
| 4,969,458 A | 11/1990 | Wiktor |
| 4,990,131 A | 2/1991 | Dardik et al. |
| 4,990,155 A | 2/1991 | Wilkoff |
| 4,994,071 A | 2/1991 | MacGregor |
| 5,015,253 A | 5/1991 | MacGregor |
| 5,035,706 A | 7/1991 | Gianturco et al. |
| 5,041,126 A | 8/1991 | Gianturco |
| 5,064,435 A | 11/1991 | Porter |
| 5,102,417 A | 4/1992 | Palmaz |
| 5,104,404 A | 4/1992 | Wolff |
| 5,116,365 A | 5/1992 | Hillstead |
| 5,122,154 A | 6/1992 | Rhodes |
| 5,131,908 A | 7/1992 | Dardik et al. |
| 5,133,732 A | 7/1992 | Wiktor |
| 5,135,536 A | 8/1992 | Hillstead |
| 5,163,958 A | 11/1992 | Pinchuk |
| 5,171,262 A | 12/1992 | MacGregor |
| 5,176,660 A | 1/1993 | Truckai |
| 5,178,618 A | 1/1993 | Kandarpa |
| 5,192,307 A | 3/1993 | Wall |
| 5,195,984 A | 3/1993 | Schatz |
| 5,217,483 A | 6/1993 | Tower |
| 5,222,971 A | 6/1993 | Willard et al. |
| 5,246,445 A | 9/1993 | Yachia et al. |
| 5,258,021 A | 11/1993 | Duran |
| 5,266,073 A | 11/1993 | Wall |
| 5,275,622 A | 1/1994 | Lazarus et al. |
| 5,282,823 A | 2/1994 | Schwartz et al. |

(List continued on next page.)

Primary Examiner—Michael J. Milano
Assistant Examiner—Tan-Uyen T. Ho

(57) ABSTRACT

Disclosed is an open cell stent that has adjacent sets of circumferential struts connected by means of highly flexible, undulating, connecting struts. To decrease outward flaring of the circumferential struts when the pre-deployed stent is advanced through highly curved vessels, each unconnected strut of the sets of circumferential struts has a decreased longitudinal length as compared to the longitudinal length of the circumferential struts that are connected by the flexible connecting struts. To decrease the propensity for outward flaring of the end set of circumferential struts, the longitudinal length of the end set of circumferential struts is shorter than the longitudinal length of the interior set of circumferential struts. Also, the attachment point of the flexible connecting struts is off the center of the curved sections of the circumferential struts, thus also decreasing the tendency for outward flaring of the end set of circumferential struts.

14 Claims, 5 Drawing Sheets

U.S. PATENT DOCUMENTS

| | | |
|---|---|---|
| 5,282,824 A | 2/1994 | Gianturco |
| 5,290,305 A | 3/1994 | Inoue |
| 5,292,331 A | 3/1994 | Boneau |
| 5,304,200 A | 4/1994 | Spaulding |
| 5,314,444 A | 5/1994 | Gianturco |
| 5,314,472 A | 5/1994 | Fontaine |
| 5,334,301 A | 8/1994 | Heinke et al. |
| 5,342,387 A | 8/1994 | Summers |
| 5,354,257 A | 10/1994 | Roubin et al. |
| 5,354,308 A | 10/1994 | Simon et al. |
| 5,366,504 A | 11/1994 | Andersen et al. |
| 5,370,683 A | 12/1994 | Fontaine |
| 5,370,691 A | 12/1994 | Samson |
| 5,375,612 A | 12/1994 | Cottenceau et al. |
| 5,376,112 A | 12/1994 | Duran |
| 5,382,261 A | 1/1995 | Palmaz |
| 5,387,235 A | 2/1995 | Chuter |
| 5,389,106 A | 2/1995 | Tower |
| 5,395,390 A | 3/1995 | Simon et al. |
| 5,397,355 A | 3/1995 | Marin et al. |
| 5,403,341 A | 4/1995 | Solar |
| 5,405,377 A | 4/1995 | Cragg |
| 5,411,549 A | 5/1995 | Peters |
| 359,802 | 6/1995 | Fontaine |
| 5,421,955 A | 6/1995 | Lau et al. |
| 5,423,885 A | 6/1995 | Williams |
| 5,441,515 A | 8/1995 | Khosravi et al. |
| 5,441,516 A | 8/1995 | Wang et al. |
| 5,443,477 A | 8/1995 | Marin et al. |
| 5,443,496 A | 8/1995 | Schwartz et al. |
| 5,443,498 A | 8/1995 | Fontaine |
| 5,443,500 A | 8/1995 | Sigwart |
| 5,449,372 A | 9/1995 | Schmaltz et al. |
| 5,449,373 A | 9/1995 | Pinchasik et al. |
| 5,449,382 A | 9/1995 | Dayton et al. |
| 5,474,563 A * | 12/1995 | Myler et al. ............... 606/108 |
| 5,496,365 A | 3/1996 | Sgro |
| 5,527,354 A | 6/1996 | Fontaine et al. |
| 5,569,295 A | 10/1996 | Lam |
| 5,591,197 A | 1/1997 | Orth et al. |
| 5,632,763 A | 5/1997 | Glastra |
| 5,643,312 A | 7/1997 | Fischell et al. |
| 5,649,952 A | 7/1997 | Lam |
| 5,653,747 A | 8/1997 | Dereume |
| 5,669,924 A | 9/1997 | Shaknovich |
| 5,697,971 A | 12/1997 | Fischell et al. |
| 5,755,734 A | 5/1998 | Richter et al. |
| 5,800,508 A | 9/1998 | Goicoechea et al. |
| 5,824,049 A | 10/1998 | Ragheb et al. |
| 5,861,027 A | 1/1999 | Trapp |
| 5,876,449 A | 3/1999 | Starck et al. |
| 5,911,754 A | 6/1999 | Kanesaka et al. |
| 6,190,403 B1 | 2/2001 | Fischell et al. |
| 6,264,688 B1 * | 7/2001 | Herklotz et al. ........... 623/1.16 |

* cited by examiner

FIG. 2 "PRIOR ART"

ULTRAFLEXIBLE OPEN CELL STENT

FIELD OF USE

This invention is in the field of stents for implantation into a vessel of a human body.

BACKGROUND OF THE INVENTION

Stents are well known medical devices that have been used for maintaining the patency of a large variety of vessels of the human body. The most frequent use is for implantation into the coronary vasculature. Although stents have been used for this purpose for more than ten years, many stent designs still lack the required flexibility and radial rigidity to provide an optimum clinical result. Another deficiency of open cell stents is that some stent struts members can flare outward (fish scaling) as the stent is advanced through a tight curve.

Most current tubular stents use a multiplicity of circumferential sets of strut members connected by either straight longitudinal connecting links or undulating longitudinal connecting links. The circumferential sets of strut members are typically formed from connecting diagonal and curved sections forming a closed ring that opens up as the stent expands to form the structural element in the stent that pushes against the arterial wall. A single strut member is defined as adjacent connected diagonal and curved sections within one of the circumferential sets of strut members.

An open cell stent is defined as a stent that has circumferential sets of strut members with most of the curved sections (crowns) that are not connected by a longitudinal connecting link to an adjacent circumferential set of strut members. In comparison, a closed cell stent has every curved section of every circumferential set of strut members, except at the distal and proximal ends of the stent, attached to a longitudinal connecting link. A strut member whose curved section is not attached to a longitudinal connecting link is defined as an unconnected strut member.

There are several "open cell" stents that are currently being marketed for the treatment of coronary stenoses. Examples of these are the Tetra stent from Guidant Corporation and the S670 stent from Medtronics, Inc. Each of these stents has a limited number of straight longitudinal connecting links to join adjacent curved sections of adjacent circumferential sets of strut members. These straight longitudinal connecting links can cause outward flaring of the end circumferential sets of strut members as the stent is bent around a curve. The interior unconnected strut members also can flare outward when the pre-deployed stent mounted on a balloon is advanced through a curved vessel such as a coronary artery. Any flared out strut can engage the vessel wall during stent delivery in a curved vessel thereby preventing the stent from reaching the site that is to be stented.

SUMMARY OF THE INVENTION

The present invention is a stent that is designed to optimize many of the operating parameters that are expected for stents in the first decade of the 21st century. Specifically, an optimum design would have the following characteristics:

I. IN THE PRE-DEPLOYED STATE
  1. excellent flexibility
  2. low profile (i.e.; small outside diameter of the stent)
  3. good radiopacity
  4. smooth outer surface
  5. no flaring of struts when advancing through curved arteries
  6. a high degree of stent retention onto the delivery catheter II. AFTER DEPLOYMENT
  1. flexible so as to conform to a curved artery
  2. radially rigid (i.e.; low recoil)
  3. good radiopacity
  4. good coverage of the vessel wall (i.e.; no plaque prolapse)
  5. side branch access without strut breakage
  6. minimal foreshortening compared to the length of the stent in its pre-deployed state Although many desirable attributes are required of the catheter that is used to deliver the stent, the scope of the present invention is limited to the design of the stent itself. However, it should be understood that the reduced foreshortening of this stent is a result of having undulating longitudinal connecting links that easily extend in their longitudinal length when the balloon onto which the stent is crimped is inflated.

To accomplish the goals listed in I. and II. above, the stent would optimally have at least two open cells around the circumference of the stent. A unique feature of the present invention is that each of the strut members whose curved sections are unconnected has a shorter longitudinal length as compared to the longitudinal length of the strut members that are connected by a longitudinal connecting link. This shorter length (optimally on the order of 0.1 mm shorter) reduces outward flaring of the unconnected strut members when the stent is advanced through highly curved vessels such as some coronary arteries. Flaring (which is sometimes called "fish-scaling") can cause the stent to engage the vessel wall as the stent is advanced through curved arteries.

Another novel feature of this stent is that the longitudinal connecting links can have an undulating shape so that they can easily expand or contract in their longitudinal length when the stent is advanced through a curved vessel. The extraordinary capability of this stent to bend easily is a combination of the fact that those curved sections of adjacent circumferential sets of strut members that are connected are connected with flexible longitudinal connecting links, and many (typically one-half) of the curved sections are unconnected. Of course, the weakest possible connection that provides the highest degree of longitudinal flexibility is no connection at all. Therefore, the combination of no connections plus the few required connections between the circumferential sets of strut members being by means of highly flexible undulating longitudinal connecting links imparts to this stent an extraordinarily high degree of longitudinal flexibility.

It should also be understood that all the strut members at each end of the stent should also have a shortened longitudinal length because the outside curved section of the end circumferential sets of strut members cannot be connected to any adjacent circumferential set of strut members. By shortening all the end strut members, end flaring of the stent as it is advanced through curved vessels can be reduced. Furthermore, the fact that the interior curved sections of each strut member at the ends of the stent either has either no connection or a flexible, undulating longitudinal connecting link connection to an inner strut members, is also desirable in preventing flaring out of the strut members at the ends of the stent. This is not the case for strut members that have a straight connection to an end circumferential strut such as shown in FIG. 5 of U.S. Pat. No. 5,759,192.

Good radiopacity for the stent is achieved by having a stainless steel stent that has a wall thickness that is at least 0.0045 inches. Another means would be to use a metal with a higher density such as tantalum with a thickness greater than 0.002 inches. A third means for obtaining improved radiopacity would be to sandwich a high density metal between two layers of stainless steel with each of the co-axial tubes having a wall thickness between 0.001 and 0.002 inches with the total wall thickness of the stent being at least 0.003 inches.

Another feature of the present invention is that the undulating longitudinal connecting links readily extend in the longitudinal direction when the balloon is inflated. Since the circumferential sets of strut members upon deployment tend to decrease in their longitudinal length, the longitudinal lengthening of the undulating longitudinal connecting links has the effect of minimizing the foreshortening of the deployed stent.

Thus an object of the present invention is to have increased longitudinal flexibility for the stent by having some curved sections of each circumferential set of strut members being unconnected to the curved sections of the adjacent circumferential set of strut members with the other curved sections being connected by highly flexible, undulating longitudinal connecting links.

Another object of the present invention is to prevent flaring of the unconnected strut members by having a shorter longitudinal length for the unconnected strut members.

Still another object of the invention is to have generally shorter longitudinal lengths for all the strut members in the circumferential sets of strut members at the stent ends to reduce the tendency for end flaring of the stent.

Still another object of the invention is to decrease the propensity of the stent to have end flaring by having each curved section of the end set of strut members either being unconnected to the curved section of the adjacent (interior) set of strut members or being connected by a highly flexible undulating longitudinal connecting link.

Still another object of the invention is to connect the flexible longitudinal connecting links to the curved section of the connected strut members at a point at or near the point where the curved section of each connected strut members is joined to the diagonal section of that connected strut member, thus further reducing the propensity for end flaring.

Still another object of the invention is to have flexible longitudinal connecting links that are adapted to readily increase their longitudinal length when the balloon is inflated; thus minimizing the extent of stent foreshortening upon stent deployment.

These and other objects and advantages of this invention will become obvious to a person of ordinary skill in this art upon reading the detailed description of this invention including the associated drawings as presented herein.

DETAILED DESCRIPTION OF THE INVENTION

Although stents are in fact thin-walled, lace-like, cylindrical tubes, they are best illustrated in the form of a flat, two-dimensional layout view as shown in FIGS. 1–5 inclusive.

Figure 1:
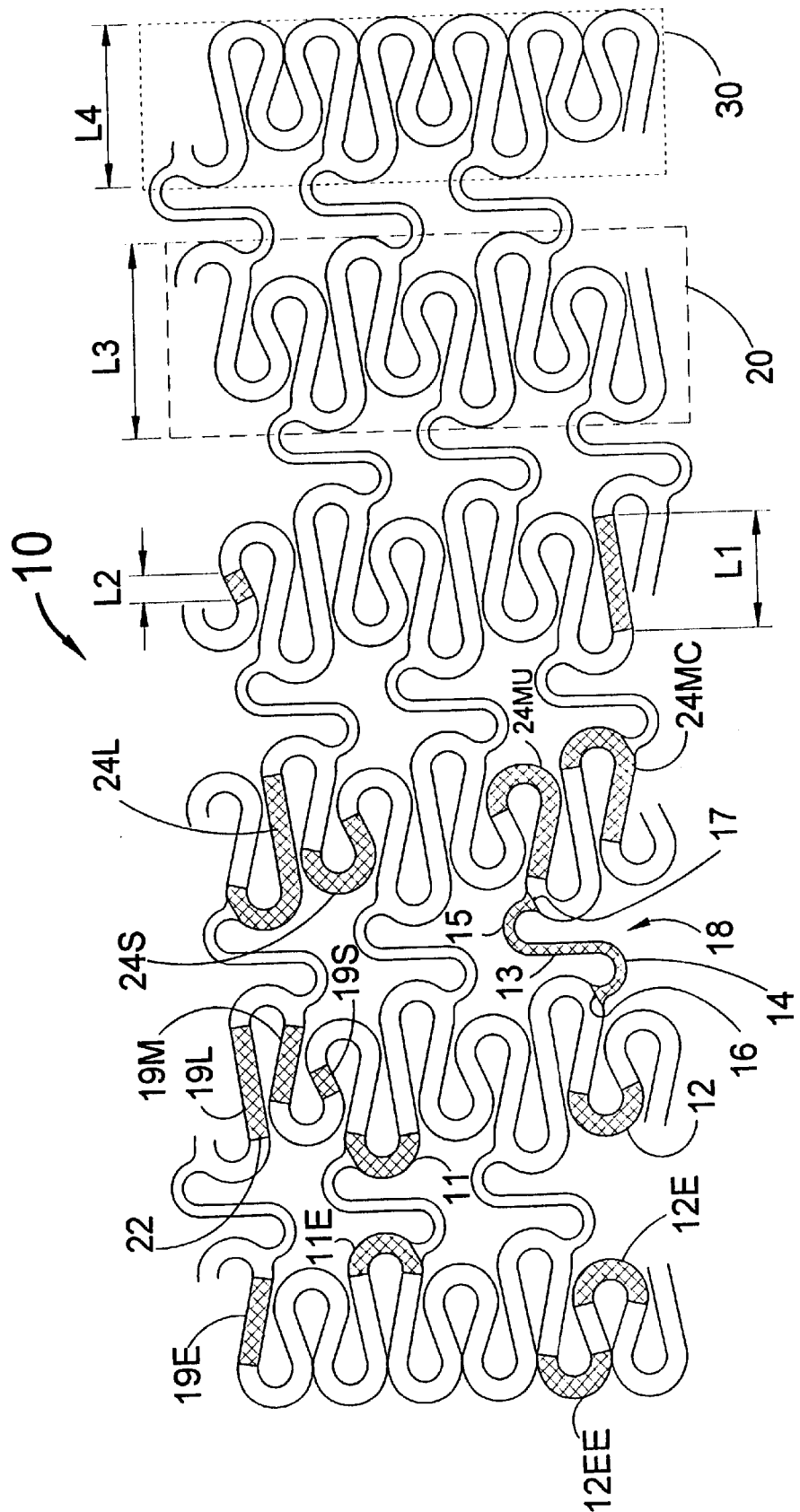
FIG. 1 is a layout view of the stent of the present invention in its pre-deployed state as it would be crimped onto the balloon of a balloon expandable stent delivery system.

FIG. 1 is a flat, layout view of a cylindrical stent 10 wherein each of the stent's top ends would be joined to each of the stent's bottom ends to form the cylindrical stent 10 in its pre-deployed, lace-like, cylindrical form.

The pre-deployed stent 10 of the present invention is shown in FIG. 1 as having a multiplicity of interior circumferential sets of strut members 20 and two end circumferential sets of strut members 30, each indicated within a dashed rectangle. For the stent 10, the connected curved sections 11 and 11E and the unconnected curved sections 12 and 12E are shown in crosshatch in FIG. 1. Also shown in crosshatch in FIG. 1 is the long diagonal section 19L, medium length diagonal section 19M and short diagonal section 19S. Each of the interior sets of strut members 20 consists of at least one long connected strut member 24L, at least one medium length connected strut member 24MC, at least one medium length unconnected strut member 24MU and at least one unconnected strut member 24S. Each of the long connected strut members 24L consists of a long diagonal section 19L joined along the line 22 to a connected curved section 11. Each medium strut member 24MC or 24MU consists of one medium diagonal section 19M connected along a line 22 to a curved section 11. Each short unconnected strut member 24S consists of a short diagonal section 19S joined to an unconnected curved section 12. As shown in FIG. 1, the longitudinal length of the long diagonal section 19L is L1 and the longitudinal length of the short diagonal section 19S is L2. As clearly seen in FIG. 1, the longitudinal length L1 is longer than the longitudinal length L2, i.e., L1>L2. For an effective stent design, L1 should be at least 0.1 mm longer than L2.

Each of the connected curved sections 11 is joined to an adjacent curved section 11 or 11E in the adjacent set of strut members by means of a longitudinally extending, flexible longitudinal connecting link 18 that consists of a central segment 13, a bottom curved segment 14 and a top curved segment 15. The bottom curved segment 14 is fixedly joined to a connected curved section 11 along the junction line 16. The top curved segment is joined to a connected Curved section 11 along the junction line 17. The optimal placement of the junction lines 16 and 17 is at or near the connecting line 22 that joins a curved section 11 (or 11E) to a diagonal section 19L, 19M or 19E. Although an "S" type flexible strut 18 is shown in FIG. 1, it should be understood that any flexible longitudinal connecting link shape that can readily lengthen or shorten in its longitudinal extent as the pre-deployed stent is advanced through a curved vessel could be used. Such flexible links are, for example, described in U.S. patent application Ser. No. 09/192,101. Thus it is anticipated that the flexible link 18 could be in the form of an "N", an inverted "N", an "M" or a "W" or any other shape (such as a "U") that can easily change its length in the longitudinal direction as the pre-deployed stent is advanced through or placed into a curved artery.

As previously stated, the unconnected diagonal sections 19S and 19M have a decreased longitudinal extent as compared to the longitudinal extent of the connected diagonal sections 19L. This design provides an open area so that the bottom curved segments 14 of the flexible longitudinal connecting links 18 do not interfere with the top curved segments 15 when the stent 10 is crimped onto a balloon of a stent delivery system. Thus a decreased profile (i.e.; smaller outer diameter) can be achieved for the pre-deployed stent 10 without causing the bottom curved segment 14 to be placed over (or beneath) the top curved segment 15.

Connected curved sections 11 do not have a tendency to flare outward when the pre-deployed stent 10 is advanced through a curved vessel because the longitudinal connecting struts 18 exert an inward radial force that tends to prevent such flaring. Therefore, one can have connected strut members 24L that are comparatively long and still they will not flare out to engage the vessel wall when the stent 10 is advanced through a curved vessel. However, without longitudinal connecting links, an unconnected curved section (such as the unconnected curved section 12) will tend to flare outward as the stent 10 is advanced around a bend in a curved vessel. To minimize such tendency to flare, the unconnected strut members 24S have a short diagonal section 19S with a reduced longitudinal length L2 as compared to the longitudinal length L1 of the diagonal section 19L of the connected strut members 24L. The unconnected medium strut member 24MU has a diagonal section 19M that has a reduced length as compared to the diagonal 19L of the long strut member 24L. A reduced length is defined herein as being at least 0.1 mm shorter than the length L1 of the long diagonal 19L. By this design, the pre-deployed stent 10 will have little or no flaring or fish-scaling for all interior curved sections of the stent 10. However, there will always be some tendency to have end flaring for each of the end curved sections 12EE of the end set of strut members 30. Reduced flaring of the end curved sections 12EE is accomplished by having comparatively short diagonal sections 19E and also by the location of the attachment line 22 where the links 18 are joined to the curved sections 11E of the end set of strut members 30. The advantageous design of the stent 10 of FIG. 1 in reducing the propensity for end flaring is best explained by first referring to FIGS. 2 and 3 that illustrate prior art stent designs that tend to have a significant propensity for end flaring.

Figure 2:
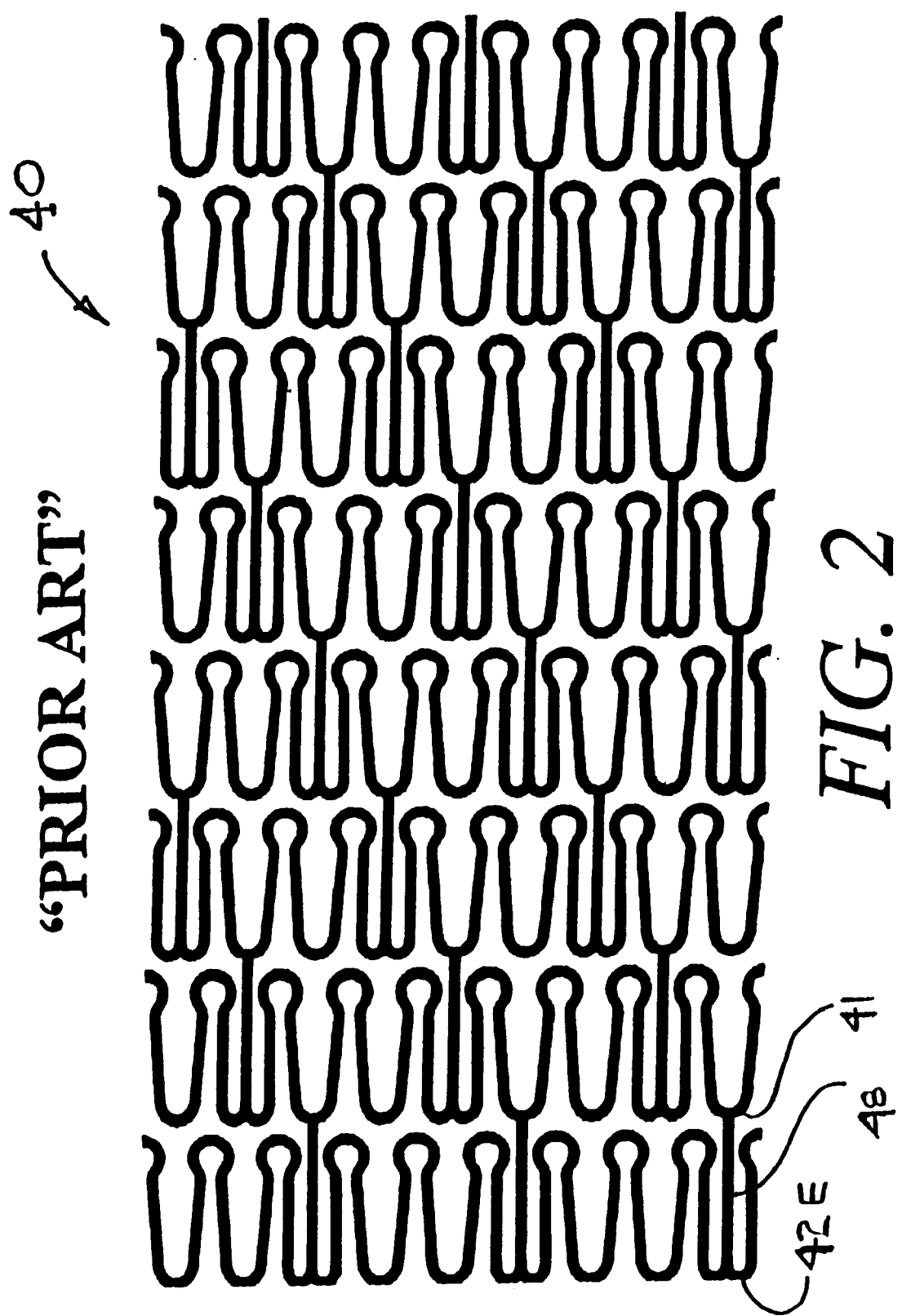
FIG. 2 is a layout view of a prior art stent showing a straight longitudinal connecting link joining the inside of a curved section of a circumferential set of strut members to the outside curved section of the adjacent circumferential set of strut members.

FIG. 2 illustrates a prior art stent design which is the Multi-Link RX Ultra marketed by Guidant Corporation. In this design, the stent 40 has an end curved section 42E that has an inside connection of a straight longitudinal connecting link 48 that connects to the outside of the interior connecting curved section 41. Because the connecting strut 48 is formed out of the wall of a straight tube, it is straight, comparatively long and it tends to remain straight as the stent 40 mounted on a balloon is advanced through a curved vessel. Thus the longitudinal connecting link 48 can actually force the end curved section 42E to flare outward in a highly curved vessel.

Figure 3:
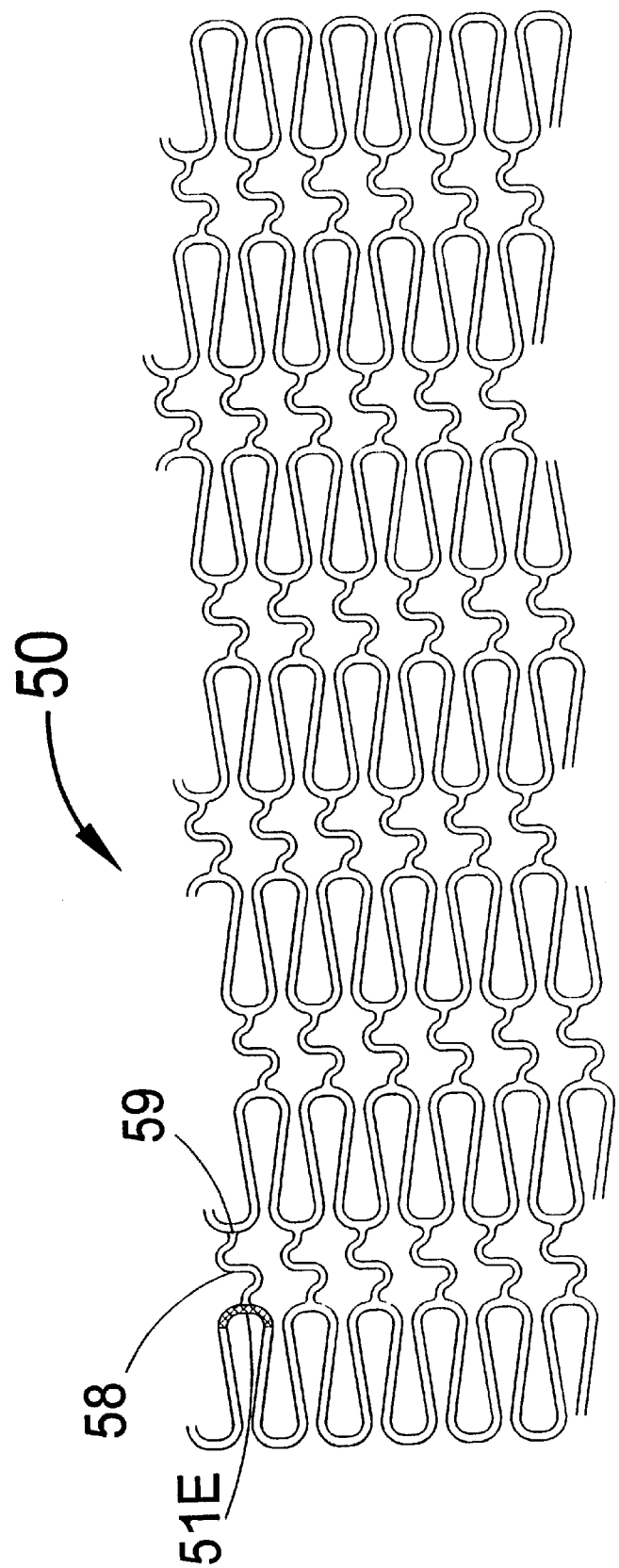
FIG. 3 is a layout view of a closed cell stent having flexible longitudinal connecting links attached at the center of the outside of all the curved sections of every circumferential set of strut members.

FIG. 3 illustrates a stent design that has an "S"-shaped connecting link 58 connected at the centered, longitudinal end point 59 to an end connected curved section 51E. Thus there is some tendency for the short, straight section of the link 58 where it joins the curved section 51E to cause the end struts of the stent 50 to flare outward. It should be understood however, that the design of FIG. 3 has a much decreased tendency for end flaring as compared to the design of FIG. 2.

Returning now to a discussion of FIG. 1, because the connection lines 16 and 17 are not at the centered, longitudinal end point of the connecting curved end section 11E, the flexible longitudinal connecting links 18 cannot exert a substantial force onto the interior end curved sections 11E to cause end flaring. In fact, because of the shape of curved sections 14 and 15, and because of their off-center attachment to the connected curved end section 11E, the longitudinal connecting strut 18 can only exert an insignificant torque onto the curved end sections 11E. Thus, the connecting links 18 do not cause any significant tendency to have any of the strut members of the end set of strut members 30 flare outward in curved vessels. Put another way, the undulating longitudinal connecting link 18 will tend to follow the curve within a curved vessel and will not have a tendency to remain straight in the longitudinal direction as is the case for the straight longitudinal connecting link 48 shown in FIG. 2. Thus the flexible longitudinal connecting link 18 has a dramatically reduced propensity to cause end flaring of the stent 10.

Another factor in decreasing end flaring (as seen in FIG. 1) is that the longitudinal length L3 of the interior sets of strut members 20 is greater by at least 0.05 mm as compared to the longitudinal length L4 of the end sets of strut members 30. Also, the attachment point for the flexible longitudinal connecting links 18 along the line 16 or 17 is such that the effective longitudinal length that can cause end flaring is even less than the length L4. For a connecting link such as the connecting link 58 of FIG. 3 that is connected at the center of an end curved section, there would be an increased tendency for end flaring as compared to the design of FIG. 1.

Figure 4:
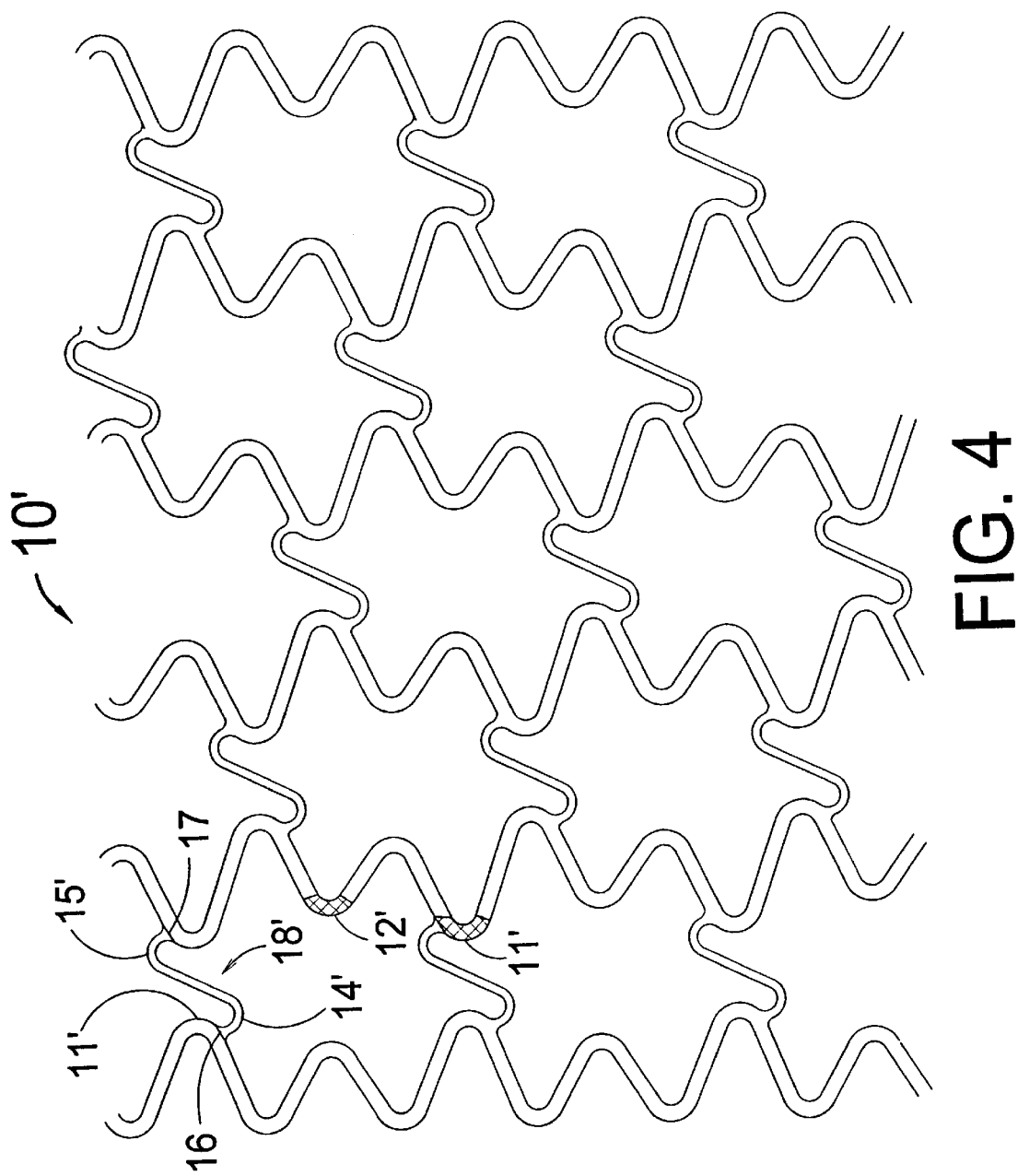
FIG. 4 is a layout view of the stent of FIG. 1 shown in its deployed state.

FIG. 4 is a flat, layout view of the deployed stent 10' showing the deployed curved sections 11' and 12' and the shape of the deployed flexible longitudinal connecting link 18' having a deployed bottom curved segment 14' and a top curved segment 15'.

Because the longitudinal length decreases for all circumferential sets of strut members 20 or 30 when the balloon on which the stent 10 is mounted is inflated, there is a tendency for the stent 10' to be foreshortened in its longitudinal length as compared to the longitudinal length of the pre-deployed stent 10. However, because the strut members 20 and 30 are firmly crimped onto the balloon, as the balloon is inflated, they have a longitudinal retention force from friction with the balloon surface that is great enough to cause the comparatively weak longitudinal connecting links 18' to lengthen in the longitudinal direction. Therefore, as the balloon is expanded, the longitudinal connecting links 18' will actually be stretched in the longitudinal direction, thus increasing their longitudinal length during balloon inflation. The effect of lengthening the longitudinal extent of the longitudinal connecting links 18' is to decrease the foreshortening of the deployed stent 10'.

Figure 5:
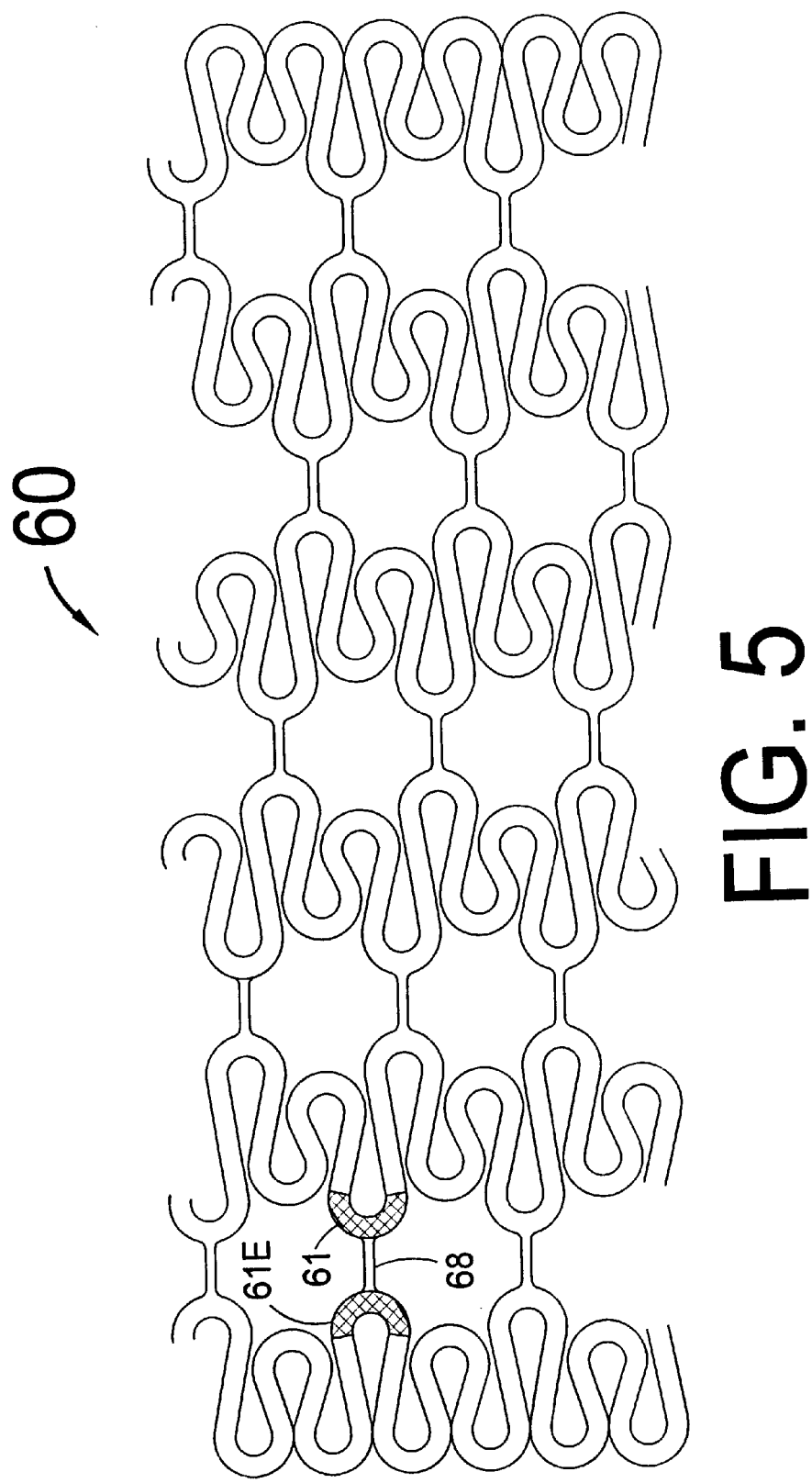
FIG. 5 is a layout view of a stent of the present invention in which alternate adjacent curved sections are connected by straight longitudinal connecting links.

Although the greatest longitudinal flexibility for the stent 10 is obtained by connecting some of adjacent sets of strut members with flexible longitudinal connecting links (like the link 18), it should be understood that short, straight links could be used to connect adjacent curved sections such as 12 and 12E of FIG. 1. This design concept is shown in FIG. 5 that is a layout view of a stent 60 that has connected curved sections 61 and 61E that are connected by straight connecting links 68. Of course it should be understood that any combination of straight and flexible longitudinal connecting links could be used. Furthermore, for any one stent, different sets of adjacent strut members could be joined by a different number and/or different type of connecting links. The number of connecting links connecting any pair of adjacent sets of strut members could be as few as one or as many as eight. The design of FIG. 5 has several advantages over the design of FIG. 2 although both use straight longitudinal connecting links to connect the circumferential sets of strut members. The stent of FIG. 5 only connects to the outsides of the curved sections 61 or 61E. For the same width of the circumferential sets of strut members this will reduce the minimum crimpable diameter of the stent 60 as compared to the stent 40 of FIG. 2 because the straight longitudinal connecting links 48 of the stent 40 separate the curved sections of some of the strut members when the stent 40 is crimped down on a balloon.

Various other modifications, adaptations and alternative designs are of course possible in light of the teachings as presented herein. Therefore it should be understood that, while still remaining within the scope and meaning of the appended claims, this invention could be practiced in a manner other than that which is specifically described herein.

What is claimed is:

1. A stent in the form of a thin-walled, lace-like, cylindrical tube with a longitudinal axis, the stent comprising:

a multiplicity of interior circumferential sets of strut members and one end circumferential set of strut members at each of the two longitudinal ends of the stent;

each interior circumferential set of strut members including at least one connected strut member consisting of a long diagonal section having a longitudinal length L1 fixedly attached to a connected curved section, each connected curved section being joined by means of a longitudinal connecting link to one connected curved section of an adjacent circumferential set of strut members and all connecting links that connect adjacent circumferential sets of strut members are connected at a connected curved section; each interior set of strut members also including at least one unconnected strut member consisting of a short diagonal section having a longitudinal length L2 fixedly joined to an unconnected curved section; and the stent being further characterized by having the length L1 of each long diagnol section being longer than the length L2 of each short diagonal section i.e.; L1<L2, so that the unconnected strut members have a decreased tendency for flaring outward as the stent is advanced though a curved vessel.

2. The stent of claim 1 wherein the longitudinal connecting link is straight.

3. The stent of claim 1 wherein the longitudinal connecting link is an undulating, flexible, longitudinal connecting link that is adapted to change its length in the longitudinal direction as the stent is advanced through a curved vessel.

4. The stent of claim 3 wherein the place where each flexible longitudinal connecting link is joined to the interior set of strut members is near the connecting line where a connected curved section is joined to a diagonal section.

5. The stent of claim 3 wherein the flexible connecting link is in the general form of an "S".

6. The stent of claim 3 wherein upon deployment to its deployed state, the flexible longitudinal connecting links extend in their longitudinal length thereby reducing the foreshortening of the stent.

7. The stent of claim 1 wherein there are at most three longitudinal connecting links that join each adjacent pair of circumferential sets of strut members.

8. The stent of claim 1 wherein there are at most five longitudinal connecting links that join each adjacent pair of circumferential sets of strut members.

9. The stent of claim 1 wherein there are at most eight longitudinal connecting links that join each adjacent pair of circumferential sets of strut members.

10. The stent of claim 1 wherein the total longitudinal length L4 in the longitudinal direction of each end circumferential set of strut members is shorter than the longitudinal length L3 in the longitudinal direction of each interior circumferential set of strut members, thus decreasing the propensity for flaring outward of the end circumferential set of strut members when the pre-deployed stent is advanced through a curved vessel.

11. The stent of claim 1 wherein the metal from which the stent is formed in stainless steel and the wall thickness of the pre-deployed stent is greater than 0.0045 inches so as to obtain acceptable radiopacity for the stent when it is being implanted into a human subject.

12. The stent of claim 1 wherein the metal from which the stent is formed is tantalum and the wall thickness of the pre-deployed stent is greater than 0.002 inches so as to obtain acceptable radiopacity for the stent when it is being implanted into a human subject.

13. The stent of claim 1 wherein the metals from which the stent is formed is a sandwich of three coaxial tubes having stainless steel as interior and exterior tubes and a central tube formed from a high density metal, the total wall thickness of the pre-deployed stent being greater than 0.003 inches so as to obtain acceptable radiopacity for the stent when it is being implanted into a human subject.

14. A stent in the form of a thin-walled, lace-like, cylindrical tube with a longitudinal axis, the stent comprising:

a multiplicity of interior circumferential sets of strut members and one end circumferential set of strut members at each of the two longitudinal ends of the stent;

each interior circumferential set of strut members including at least one connected strut member consisting of a long diagonal section having a longitudinal length L1 fixedly attached to a connected curved section, each connected curved section of an adjacent means of a longitudinal connecting link to one connected curved section of an adjacent circumferential set of strut members; each interior set of strut members also including at least one unconnected strut member consisting of a short diagonal section having a longitudinal length L2 fixedly joined to an unconnected curved section; and the stent being further characterized by having the length L1 of each diagonal section being longer than the length L2 of each short diagonal section and for each interior circumferential set of strut members, the number of connected curved sections being equal to the number of unconnected curved sections.

* * * * *

UNITED STATES PATENT AND TRADEMARK OFFICE
CERTIFICATE OF CORRECTION

PATENT NO. : 6,540,775 B1
DATED : April 1, 2003
INVENTOR(S) : Robert E. Fischell, David R. Fischell and Tim A. Fischell It is certified that error appears in the above-identified patent and that said Letters Patent is hereby corrected as shown below:

Title page, Item [54] and Column 1, line 1,
Please delete the words "OPEN CELL" and replace with the word -- HYBRID -- so that the title should read -- ULTRAFLEXIBLE HYBRID STENT --.

Column 1,
Line 39, ending with the words, "unconnected strut member", add the following sentence:
-- A hybrid stent is defined herein as having interior circumferential sets of strut members that have an equal number of connected and unconnected curved sections. --

Column 7,
Line 41, please delete "diagnol" and replace with -- diagonal --.

Column 8,
Lines 36-59, claim 14 should read:
14. A stent in the form of a thin-walled, lace-like, cylindrical tube with a longitudinal axis, the stent comprising:
    a multiplicity of interior circumferential sets of strut members and one end circumferential set of strut members at each of the two longitudinal ends of the stent;
    each interior circumferential set of strut members including at least one connected strut member consisting of a long diagonal section having a longitudinal length L1 fixedly attached to a connected curved section, each connected curved section being joined by means of a longitudinal connecting link to one connected curved section of an adjacent circumferential set of strut members; each interior set of strut members also including at least one unconnected strut member consisting of a short diagonal section having a longitudinal length L2 fixedly joined to an unconnected curved section; and

UNITED STATES PATENT AND TRADEMARK OFFICE
CERTIFICATE OF CORRECTION

PATENT NO.    : 6,540,775 B1
DATED         : April 1, 2003
INVENTOR(S)   : Robert E. Fischell, David R. Fischell and Tim A. Fischell It is certified that error appears in the above-identified patent and that said Letters Patent is hereby corrected as shown below:

Column 8 (cont'd),
    the stent being further characterized by having the length L1 of each diagonal section being longer than the length L2 of each short diagonal section and for each interior circumferential set of strut members, the number of connected curved sections being equal to the number of unconnected curved sections.

Signed and Sealed this

Twelfth Day of August, 2003

JAMES E. ROGAN
*Director of the United States Patent and Trademark Office*